(12) United States Patent
Tsutsumi

(10) Patent No.: US 9,970,375 B2
(45) Date of Patent: May 15, 2018

(54) DEVICE FOR DETECTING THAT FUEL SHUT-OFF VALVE IS STUCK CLOSED

(71) Applicant: HINO MOTORS, LTD., Hino-shi (JP)

(72) Inventor: Munechika Tsutsumi, Tokyo (JP)

(73) Assignee: HINO MOTORS, LTD., Hino-shi (JP)

( * ) Notice: Subject to any disclaimer, the term of this patent is extended or adjusted under 35 U.S.C. 154(b) by 102 days.

(21) Appl. No.: 14/888,548

(22) PCT Filed: Jul. 8, 2014

(86) PCT No.: PCT/JP2014/068179
§ 371 (c)(1),
(2) Date: Nov. 2, 2015

(87) PCT Pub. No.: WO2015/005337
PCT Pub. Date: Jan. 15, 2015

(65) Prior Publication Data
US 2016/0061136 A1    Mar. 3, 2016

(30) Foreign Application Priority Data

Jul. 10, 2013   (JP) ................................. 2013-144156

(51) Int. Cl.
F02D 41/22     (2006.01)
F02D 41/02     (2006.01)
G01N 15/06     (2006.01)

(52) U.S. Cl.
CPC .......... F02D 41/221 (2013.01); G01N 15/06 (2013.01); F02D 41/029 (2013.01); F02D 2041/224 (2013.01); F02D 2200/0602 (2013.01); F02D 2200/0604 (2013.01); Y02T 10/40 (2013.01)

(58) Field of Classification Search
CPC ................. F02D 41/221; F02D 41/029; F02D 2041/224; F02D 2200/0602; F02D 2200/0604; Y02T 10/40; G01N 15/06
See application file for complete search history.

(56) References Cited

U.S. PATENT DOCUMENTS 4,606,312 A  *  8/1986  Nakano ................. G01M 15/08
                                                      123/198 DB
2007/0251502 A1*  11/2007  Takayanagi .......... F02D 41/222
                                                      123/458
2012/0156056 A1    6/2012  Akita

FOREIGN PATENT DOCUMENTS

JP    2002-38940 A      2/2002
JP    2002038940 A  *  2/2002
JP    2002-129945 A     5/2002
(Continued)

OTHER PUBLICATIONS

International search report dated Oct. 7, 2014 in PCT/JP2014/068179 filed Jul. 8, 2014.*

Primary Examiner — R. A. Smith
Assistant Examiner — John M Royston
(74) Attorney, Agent, or Firm — Oblon, McClelland, Maier & Neustadt, L.L.P.

(57) ABSTRACT

Disclosed is a device for detecting any fixed closure of a fuel shut-off valve 7 which opens/closes a feed line 5 for feed of fuel 3 to a fuel addition valve 6. The device is provided with a pressure sensor 8 which detects a pressure of the fuel 3 between the fuel addition and shut-off valves 6 and 7 and a controller 9 which determines the fuel shut-off valve 7 to be fixed closed when a detection value of the pressure sensor 8 falls below a threshold set depending on a rotation frequency of an engine.

4 Claims, 1 Drawing Sheet

(56) References Cited

FOREIGN PATENT DOCUMENTS

| | | |
|---|---|---|
| JP | 2003-193824 A | 7/2003 |
| JP | 2012-127316 A | 7/2012 |

* cited by examiner

DEVICE FOR DETECTING THAT FUEL SHUT-OFF VALVE IS STUCK CLOSED

TECHNICAL FIELD

The present invention relates to a device for detecting any fixed closure of a fuel shut-off valve.

BACKGROUND ART

Particulates (particulate matter) contained in exhaust gas from a diesel engine are mainly constituted by carbonic soot and a soluble organic fraction (SOF) of high-boiling hydrocarbon and contain a trace of sulfate (misty sulfuric acid fraction). In order to reduce such particulates, conventionally a particulate filter has been incorporated in an exhaust pipe through which exhaust gas flows.

Such particulate filter has a porous honeycomb structure made of ceramics such as cordierite and having lattice-like compartmentalized passages; alternate ones of the passages have plugged inlets and the remaining passages with unplugged open inlets have plugged outlets. Only the exhaust gas passing through thin porous walls compartmentalizing the passages is discharged downstream.

The particulates in the exhaust gas, which are captured and accumulated on inner surfaces of the thin porous walls, require to be burned off for regeneration of the particulate filter before exhaust resistance increases due to clogging. However, the exhaust from the diesel engine in a normal operation status has little chance to reach a temperature level at which the particulates ignite by themselves.

In order to overcome this, an oxidation catalyst comprising alumina carrying platinum and added with an appropriate amount of rare earth element such as cerium is integrally carried by a particulate filter. The oxidation catalyst facilitates an oxidation reaction of particulates captured by the particulate filter to lower the ignition temperature, so that the particulates can be burned off even at an exhaust temperature level lower than ever before.

However, even in such a case, a captured amount of the particulates may exceed a treated amount in an operation area having a lower exhaust temperature level. Continued operation at such lower exhaust temperature level may hinder sufficient regeneration of the particulate filter, resulting in excessive accumulation of the captured particulates in the particulate filter. Thus, when an amount of accumulated particulates has increased, it is necessary to forcibly heat the particulate filter to burn off the captured particulates.

More specifically, it has been conceived that a flow-through type oxidation catalyst is arranged in front of the particulate filter and a fuel addition valve is incorporated in the exhaust pipe upstream of the oxidation catalyst and that fuel added by the fuel addition valve is caused to make oxidization reaction through the oxidation catalyst and the exhaust gas elevated in temperature by resultant reaction heat is guided to the particulate filter to increase a catalyst bed temperature to thereby burn off the particulates, resulting in regeneration of the particulate filter.

With respect to this kind of forced regeneration of a particulate filter, there exists, for example, Patent Literature 1 by the applicant same as that of the present invention.

CITATION LIST

Patent Literature

Patent Literature 1: JP 2003-193824A

SUMMARY OF INVENTION

Technical Problems

Recently obliged in countries is equipment of a so-called on-board diagnosis device (OBD) to a vehicle to monitor any failure in an exhaust gas countermeasure system; upon failure occurrence, it turns on a warning light or the like for announcement of the failure occurrence to a driver and records details of the failure. A diagnosis for failure has been desired to be conducted also for a fuel shut-off valve incorporated in a feed line for feed of fuel to the fuel addition valve.

Specifically, the feed line for feed of the fuel to the fuel addition valve is provided with the fuel shut-off valve adapted to be instantly energized to open upon key-on operation and adapted to surely shut off the feed of the fuel to the fuel addition valve upon key-off operation. When a moving part of the fuel shut-off valve is fixed closed due to, for example, foreign matter caught by the moving part, the fuel cannot be fed to the fuel addition valve upon key-on operation, failing in fuel addition, for example, for regeneration of the particulate filter.

The invention was made in view of the above and has its object to enable detection of any fixed closure of a fuel shut-off valve which opens/closes a feed line for feed of fuel to a fuel addition valve.

Solution to Problems

The invention is directed to a device for detecting any fixed closure of a fuel shut-off valve which opens/closes a feed line for feed of fuel to a fuel addition valve characterized in that it comprises a pressure sensor for detecting a pressure of the fuel between said fuel addition and shut-off valves and a controller for determining said fuel shut-off valve to be fixed closed when a detection value by said pressure sensor is lower than a threshold set depending upon a rotation frequency of an engine.

As a result, when the fuel shut-off valve is fixed closed due to, for example, foreign matter being caught by the fuel shut-off valve, the fixed closure blocks reaching of the fuel to a downstream side of the fuel shut-off valve to thereby extremely lower a pressure of the fuel between the fuel shut-off and addition valves, which appears as a phenomenon that a detection value by the pressure sensor falls below the threshold. Perception of the phenomenon by the controller enables determination that the fuel shut-off valve is fixed closed.

In the invention, the controller is preferably adapted to determine the fuel shut-off valve to be normal when a deviation between the detection value by the pressure sensor and a fuel pressure predicted from the rotation frequency of the engine is within an allowable range and determine said pressure sensor to have characteristic abnormality when determination based on the detection value by said pressure sensor is neither normality nor fixed closure of said fuel shut-off valve.

Specifically, it has been known that when the fuel shut-off valve is normally open, the fuel pressure between the fuel addition and shut-off valves is proportional to a rotation frequency of the fuel pump and thus to the rotation frequency of the engine driving the fuel pump, so that the detection value by the pressure sensor can be predicted from the rotation frequency of the engine.

If the pressure sensor is normal, then the deviation between the detection value by the pressure sensor and the pressure of the fuel predicted from the rotation frequency of the engine is to be not substantial; if the deviation between the detection value by the pressure sensor and the predicted fuel pressure is within the allowable range, the fuel shut-off valve can be determined to be normal.

If the determination based on the detection value by the pressure sensor is neither normality nor fixed closure of the fuel shut-off valve, then it cannot be considered other than characteristic abnormality of the pressure sensor due to, for example, aged deterioration. Thus, the controller determines the pressure sensor to have characteristic abnormality.

When the pressure sensor has fundamental failure due to, for example, breaking of wire, it is usual that an extreme voltage value is instantly detected upon key-on operation, leading to determination of the failure. Such determination of the failure upon key-on operation has been well-known in the art.

Advantageous Effects of Invention

A device for detecting any fixed closure of a fuel shut-off valve according to the invention can exhibit the following various excellent effects.

(I) Even if the fuel shut-off valve is fixed closed due to, for example, foreign matter being caught by the fuel shut-off valve, the fixed closure can be detected as a phenomenon that the fuel pressure between the fuel shut-off and addition valves is extremely lowered, resulting in the detection value by the pressure sensor falling below the threshold. Thus, preliminarily prevented is a trouble that the fuel is not actually added irrespective of a command on fuel addition by the fuel addition valve.

(II) By adapting the controller to determine the fuel shut-off valve to be normal when a deviation between the detection value by the pressure sensor and the fuel pressure predicted from the rotation frequency of the engine is within an allowable range and determine said pressure sensor to have characteristic abnormality when the determination on the basis of the detection value by said pressure sensor is neither normality nor fixed closure of said fuel shut-off valve, not only fixed closure of the fuel shut-off valve but also whether the pressure sensor is normal or has characteristic abnormality can be determined. Thus, health of the pressure sensor can be diagnosed in addition to any fixed closure of the fuel shut-off valve.

DESCRIPTION OF EMBODIMENT

Figure 1:
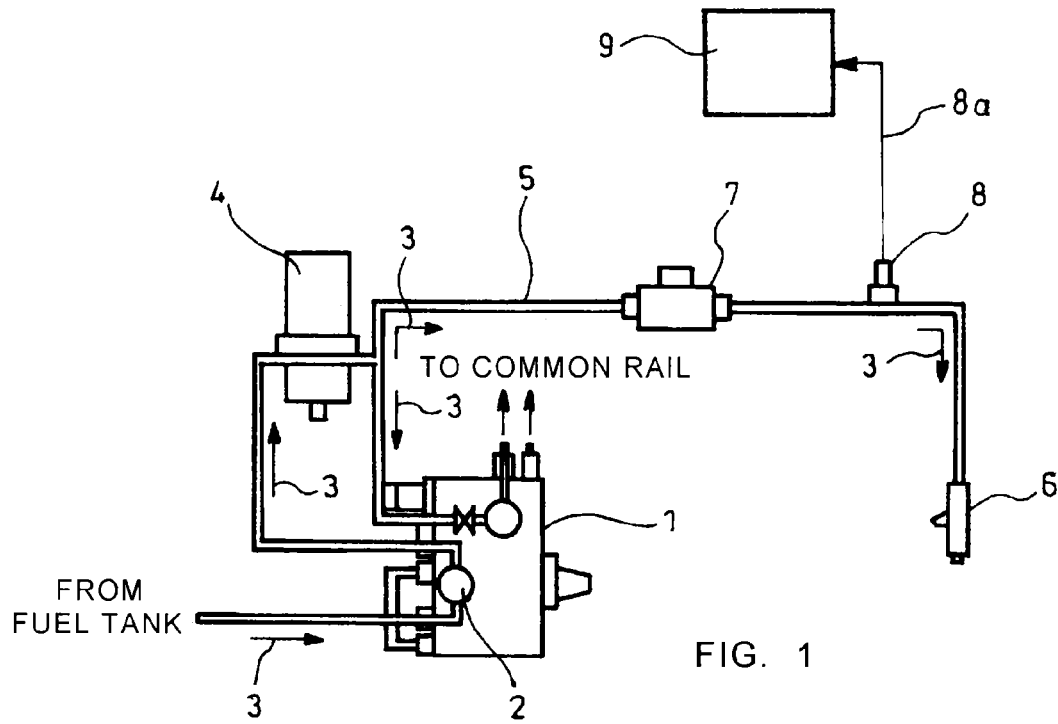
FIG. 1 is a schematic diagram showing an embodiment of the invention.

Next, an embodiment of the invention will be described in conjunction with the drawing.

FIG. 1 shows an embodiment of the invention in which reference numeral 1 denotes a fuel pump driven by an engine (not shown). The fuel pump 1 is provided with a feed pump 2 driven by a cam shaft same as that for the fuel pump 1 to introduce and pass fuel 3 from a fuel tank (not shown) and through a fuel filter 4 for filtration of solid materials into the fuel pump 1. The fuel 3 pressurized into high pressure in the fuel pump 1 is fed under pressure to a common rail (not shown). Part of the fuel 3 from the fuel filter 4 to the fuel pump 1 is guided through a feed line 5 to a fuel addition valve 6. Incorporated in the feed line 5 is a fuel shut-off valve 7 which opens/closes the feed line 5.

The fuel addition valve 6 is arranged in an exhaust pipe upstream of an oxidation catalyst which in turn is in front of a particulate filter (not shown), and conducts fuel addition for regeneration of the particulate filter in a step that accumulated particulates have increased in the particulate filter. The added fuel 3 is caused to make an oxidization reaction through the oxidation catalyst and the exhaust gas increased in temperature due to resultant reaction heat is introduced into the particulate filter to increase a catalyst bed temperature. As a result, the particulates are burnt out to attain regeneration of the particulate filter.

In the embodiment, arranged between the fuel addition and shut-off valves 6 and 7 is a pressure sensor 8 which detects a pressure of the fuel 3, a detection signal 8a from the pressure sensor 8 being inputted to a controller 9. The controller 9 determines the fuel shut-off valve 7 to have fixed closure when a detection value by the pressure sensor 8 falls below a threshold set depending on a rotation frequency of an engine.

Figure 2:
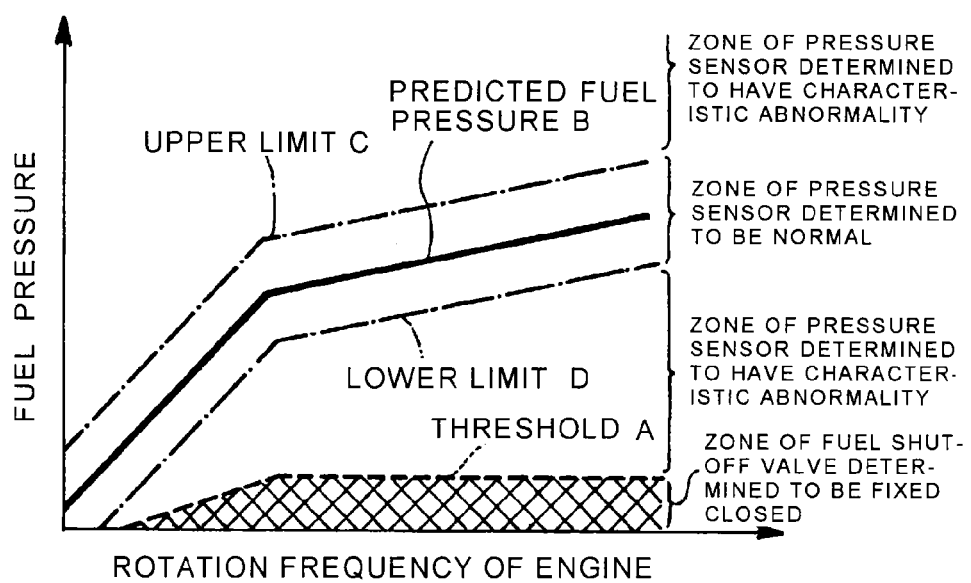
FIG. 2 is a graph showing an example of a control map used for the controller shown in FIG. 1.

Specifically, a control map as shown in FIG. 2 on fuel pressure (detection value by the pressure sensor 8) and rotation frequency of engine is incorporated in the controller 9. In the control map, a zone (crosshatched portion) where a detection value by the pressure sensor 8 falls below a threshold A set depending on the rotation frequency of the engine is defined as a zone of the fuel shut-off valve 7 determined to be fixed closed.

In this connection, it has been revealed that, when the fuel shut-off valve 7 is normally open, the pressure of the fuel 3 between the fuel addition and shut-off valves 6 and 7 is proportional to a rotation frequency of the fuel pump 1 and thus to a rotation frequency of the engine driving the fuel pump 1, so that a detection value by the pressure sensor 8 can be predicated from the rotation frequency of the engine shown in the control map of FIG. 2 as predicted fuel pressure B. Then, by properly setting an extremely low threshold A greatly falling below the predicted fuel pressure B, the fuel shut-off valve 7 can be regarded to be fixed closed when the detection value by the pressure sensor 8 falls below the threshold A.

Further in the embodiment, when the deviation between the detection value by the pressure sensor 8 and the predicted fuel pressure B is within an allowable range, the fuel shut-off valve 7 is determined to be normal; when the determination based on the detection value by the pressure sensor 8 is neither normality nor fixed closure of the fuel shut-off valve 7, the pressure sensor 8 is determined to have characteristic abnormality. More specifically, regarded as a zone of the pressure sensor 8 determined to be normal is a zone defined by upper and lower limits C and D with positive and negative allowable deviations to the predicted fuel pressure B, respectively; and regarded as zones of the pressure sensor 8 determined to have characteristic abnormality are zones other than the zone of the pressure sensor 8 determined to be normal and the zone of the fuel shut-off valve 7 determined to be fixed closed (the zones above and below the zone of the pressure sensor 8 determined to be normal are higher- and lower-pressure-side zones determined to have characteristic abnormality, respectively).

As a result, when the fuel shut-off valve 7 has fixed closed due to, for example, foreign matter being caught by the fuel shut-off valve 7, the fixed closure blocks reaching of the fuel 3 to a downstream side of the fuel shut-off valve 7 to thereby extremely lower a pressure of the fuel 3 between the fuel shut-off and addition valves 7 and 6, which appears as a phenomenon that a detection value by the pressure sensor 8 falls below the threshold A. Perception of the phenomenon by the controller 9 enables determination that the fuel shut-off valve 7 is fixed closed.

Moreover, when the pressure sensor 8 is normal, then the detection value by the pressure sensor 8 is to have no substantial deviation to the predicted fuel pressure B on the basis of the engine rotation frequency. Thus, if the deviation between the detection value by the pressure sensor 8 and the predicted fuel pressure B is within the allowable range, then the fuel shut-off valve 7 can be determined to be normal.

When the determination based on the detection value by the pressure sensor 8 is neither normality nor fixed closure of the fuel shut-off valve 7, then it cannot be considered other than characteristic abnormality of the pressure sensor 8 due to, for example, aged deterioration. Thus, the controller 9 determines the pressure sensor 8 to have characteristic abnormality.

When the pressure sensor 8 has a fundamental failure due to, for example, breaking of wire, it is usual that an extreme voltage value is instantly detected upon key-on operation, leading to determination of the failure. Such determination of the failure upon key-on operation has been well-known in the art.

Thus, according to the above embodiment, even if the fuel shut-off valve 7 is fixed closed due to, for example, foreign matter being caught by the fuel shut-off valve 7, the fixed closure can be detected as a phenomenon that the pressure of the fuel 3 between the fuel shut-off and addition valves 7 and 6 is extremely lowered and the detection value by the pressure sensor 8 falls below the threshold A. As a result, preliminarily prevented is a trouble that the fuel 3 is not actually added irrespective of a command of fuel addition by the fuel addition valve 6. Moreover, not only the fixed closure of the fuel shut-off valve 7 but also whether the pressure sensor 8 is normal or has characteristic abnormality can be determined. That is, the health of the pressure sensor 8 can be diagnosed together with the fixed closure of the fuel shut-off valve 7.

It is to be understood that a device for detecting any fixed closure of the invention is not limited to the above embodiment and that various changes and modifications may be made without departing from the scope of the invention. For example, though disclosed in the explanation on the specific embodiment is a case where the aftertreatment device is a particulate filter, the invention is similarly applicable to a fuel addition valve in a case where the aftertreatment device is, for example, a selective reduction catalyst with a property of selectively reacting $NO_x$ with a reducing agent even in the presence of oxygen or a $NO_x$ storage reduction catalyst with a property of oxidizing $NO_x$ in the exhaust gas when an air-fuel ratio in the exhaust is lean to temporarily store the same in the form of nitrate salt and resolving and discharging $NO_x$ through the intervention of, for example, unburned HC and CO for reduction and purification when a concentration of oxygen in the exhaust gas lowers.

REFERENCE SIGNS LIST

3 fuel
5 feed line
6 fuel addition valve
7 fuel shut-off valve
8 pressure sensor
8a detection signal
9 controller

The invention claimed is:

1. A device for detecting any fixed closure of a fuel shut-off valve which opens/closes a feed line for feed of fuel to a fuel addition valve, comprising:
   a pressure sensor for detecting a pressure of the fuel between said fuel addition and shut-off valves; and
   a controller for determining said fuel shut-off valve to be fixed closed when a detection value by said pressure sensor is lower than a threshold that varies based on a rotation frequency of an engine.

2. The device for detecting any fixed closure of the fuel shut-off valve as claimed in claim 1,
   wherein the controller is adapted to determine the fuel shut-off valve to be normal when a deviation between the detection value by the pressure sensor and a predicted fuel pressure based on the rotation frequency of the engine is within an allowable range and to determine said pressure sensor to have characteristic abnormality when determination based on the detection value by said pressure sensor is neither normal nor fixed closed.

3. The device for detecting any fixed closure of the fuel shut-off valve as claimed in claim 1,
   wherein the threshold increases when the rotation frequency of the engine increases.

4. The device for detecting any fixed closure of the fuel shut-off valve as claimed in claim 2,
   wherein the threshold to determine that said pressure valve is fixed closed is less than a detection value that determines that said pressure valve has the characteristic abnormality.

* * * * *